United States Patent
Roger et al.

(10) Patent No.: US 6,235,057 B1
(45) Date of Patent: May 22, 2001

(54) METHOD FOR SOFT TISSUE RECONSTRUCTION

(75) Inventors: Gregory James Roger; Leo Arieh Pinczewski, both of Crows Nest (AU)

(73) Assignee: Smith & Nephew, Inc., Memphis, TN (US)

(*) Notice: Subject to any disclaimer, the term of this patent is extended or adjusted under 35 U.S.C. 154(b) by 0 days.

(21) Appl. No.: 08/801,240

(22) Filed: Feb. 19, 1997

Related U.S. Application Data

(63) Continuation of application No. 08/614,904, filed on Mar. 13, 1996, now abandoned, which is a continuation of application No. 08/378,246, filed on Jan. 24, 1995, now abandoned.

(51) Int. Cl.[7] .................................................. A61F 2/08

(52) U.S. Cl. ................ 623/13.12; 606/73; 623/13.14; 623/13.17

(58) Field of Search .............................. 623/13; 606/104, 606/73

(56) References Cited

U.S. PATENT DOCUMENTS

| | | |
|---|---|---|
| 2,242,003 | 5/1941 | Lorenzo . |
| 2,267,925 | 12/1941 | Johnston . |
| 4,463,753 | 8/1984 | Gustilo . |

(List continued on next page.)

FOREIGN PATENT DOCUMENTS

| | | | |
|---|---|---|---|
| 14615-28 | 7/1928 | (AU) . | |
| 59999/90 | 2/1991 | (AU) . | |
| 2529669 | * 3/1976 | (DE) | ........................................ 623/13 |

(List continued on next page.)

OTHER PUBLICATIONS

Steiner et al., Anterior Cruciate Ligament Graft Fixation, The American Journal of Sports Medicine, (22) 2:240–247.*
European Patent Abstracts, Week 9240, p. 235, EP 506420–A1.

(List continued on next page.)

*Primary Examiner*—David H. Willse
(74) *Attorney, Agent, or Firm*—Fish & Richardson P.C.

(57) ABSTRACT

A method for the reconstruction of the anterior cruciate ligament of a patient is described. The process comprises the steps of:

1) harvesting from the patient semitendonosus and gracilis tendons, or other suitable tendons of adequate length, to form a tendon graft;
2) forming a hole through the patient's femur from the intercondylar notch therein anteriorly and laterally;
3) enlarging the cross-sectional area of that femoral hole adjacent the notch sufficiently to receive one end of the tendon graft and a suitable screw;
4) forming a suitably positioned hole through the patient's tibia opening at one end adjacent the medial tibial spine and having a cross-sectional area sufficient to receive the other end of the tendon graft and a suitable screw;
5) drawing the one end of the tendon graft through the tibial hole and the joint into the femoral hole while leaving the other end of the tendon graft in the tibial hole;
6) inserting a suitable screw into the femoral hole from its intercondylar notch end until the head of the screw is just within that end of the hole and the screw is pressing the tendon graft directly and firmly against a sidewall of the femoral hole; and
7) after tensioning the tendon graft, inserting a suitable screw into the hole in the tibia externally until the head of the screw is within the exterior end of the tibial hole and the screw is pressing the tendon graft directly and firmly against a sidewall of the tibial hole.

41 Claims, 4 Drawing Sheets

U.S. PATENT DOCUMENTS

| | | |
|---|---|---|
| 4,537,185 | 8/1985 | Stednitz . |
| 4,744,793 | 5/1988 | Parr et al. . |
| 4,772,286 * | 9/1988 | Goble et al. ............................ 623/13 |
| 4,775,380 * | 10/1988 | Seedham et al. ...................... 623/12 |
| 4,828,562 | 5/1989 | Kenna . |
| 4,870,957 | 10/1989 | Goble et al. . |
| 4,927,421 * | 5/1990 | Goble et al. . |
| 4,950,270 | 8/1990 | Bowman et al. . |
| 4,950,271 | 8/1990 | Lewis et al. . |
| 4,988,351 | 1/1991 | Paulos et al. . |
| 5,084,050 | 1/1992 | Draenert . |
| 5,116,337 | 5/1992 | Johnson . |
| 5,129,902 | 7/1992 | Goble et al. . |
| 5,129,906 | 7/1992 | Ross et al. . |
| 5,139,520 * | 8/1992 | Rosenberg ............................ 623/13 |
| 5,209,753 | 5/1993 | Biedermann et al. . |
| 5,211,647 * | 5/1993 | Schmieding ......................... 606/104 |
| 5,246,441 | 9/1993 | Ross et al. . |
| 5,258,040 * | 11/1993 | Bruchman et al. .................... 623/66 |
| 5,281,422 * | 1/1994 | Badylak et al. .................. 623/13 X |
| 5,356,435 | 10/1994 | Thein . |
| 5,383,878 | 1/1995 | Roger et al. . |
| 5,425,767 | 6/1995 | Steininger et al. . |
| 5,443,468 | 8/1995 | Johnson . |
| 5,443,509 * | 8/1995 | Boucher et al. ....................... 623/16 |
| 5,454,811 * | 10/1995 | Huebner . |
| 5,456,685 * | 10/1995 | Huebner . |
| 5,470,334 | 11/1995 | Ross et al. . |
| 5,628,766 | 5/1997 | Johnson . |
| 5,632,748 * | 5/1997 | Beck et al. ............................ 606/89 |
| 5,674,224 * | 10/1997 | Howell et al. ........................ 606/88 |

FOREIGN PATENT DOCUMENTS

| | | |
|---|---|---|
| 27 47 312 | 1/1979 | (DE) . |
| 28 18 254 | 10/1979 | (DE) . |
| 0 172 130 A2 | 2/1986 | (EP) . |
| 0 241 792 A1 | 10/1987 | (EP) . |
| 0260970 | 3/1988 | (EP) . |
| 0 282 789 A2 | 9/1988 | (EP) . |
| 0 317 406 A1 | 5/1989 | (EP) . |
| 0 374 088 A1 | 6/1990 | (EP) . |
| 451932A1 | 4/1991 | (EP) . |
| 0 506 213 A1 | 9/1992 | (EP) . |
| 0 506 420 A1 | 9/1992 | (EP) . |
| 2 622 790 | 5/1989 | (FR) . |
| 0 655 840 | 6/1991 | (FR) . |
| FR 2 663 837 | 1/1992 | (FR) . |
| 2687911 * | 9/1993 | (FR) ...................................... 623/13 |
| 2688689 * | 9/1993 | (FR) ...................................... 623/13 |
| 2 704 140 A3 * | 10/1994 | (FR) ...................................... 623/13 |
| 5300917 * | 11/1993 | (JP) ....................................... 623/13 |
| SU 1600752 A1 | 10/1990 | (SU) . |
| WO89/09030 | 10/1989 | (WO) . |
| 90/08510 | 8/1990 | (WO) . |
| WO90/08510 | 8/1990 | (WO) . |
| 9203980 * | 3/1992 | (WO) ................................... 623/13 |

OTHER PUBLICATIONS

European Patent Abstracts, Week 9240, p. 189, EP 506213–A1.

European Patent Abstracts, Week 9237, p. 161, EP 502698–A1.

European Patent Abstracts, Week 9212, p. 267, EP 475–889–A.

European Patent Abstracts, Week 9208, p. 99, EP 471–419–A.

European Patent Abstracts, Week 9206, p. 99, EP 469–441–A.

European Patent Abstracts, Week 9144, p. 250, EP 454–601–A.

European Patent Abstracts, Week 9143, p. 28, EP 452–442–A.

European Patent Abstracts, Week 9106, p. 29, EP 411–109–A.

European Patent Abstracts, Week 9118, p. 74, EP 424–734–A.

European Patent Abstracts, Week 9133, p. 77, EP 440–991–A.

European Patent Abstracts, Week 9133, EP 441–065–A.

European Patent Abstracts, Week 9134, p. 177, EP 442–629–A.

Kurosaka M. et al., Am. Journal of Sports Med., vol. 15, No. 3 pp 225–229, "A Biochemical Comparison of Different Surgical Techniques of Graft Fixation in Anterior Cruciate Ligament Reconstruction" (1987).

Lambert K.L., Clinical Orthopedics and Related Research No. 72, Jan/Feb 1983, pp 85–89, "Vascularized Patella Tendon Graft with Rigid Internal Fixation for Anterior Cruciate Ligament Insufficiency".

English Translation of French Patent No. 2 688 689.

* cited by examiner

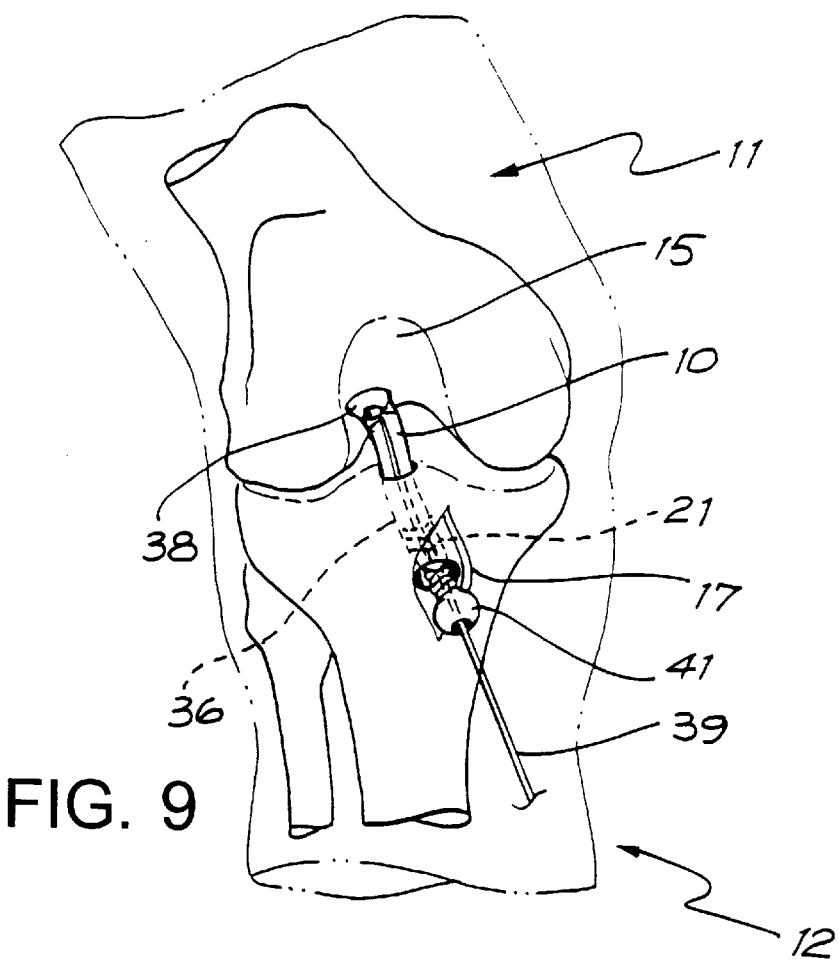
FIG. 9
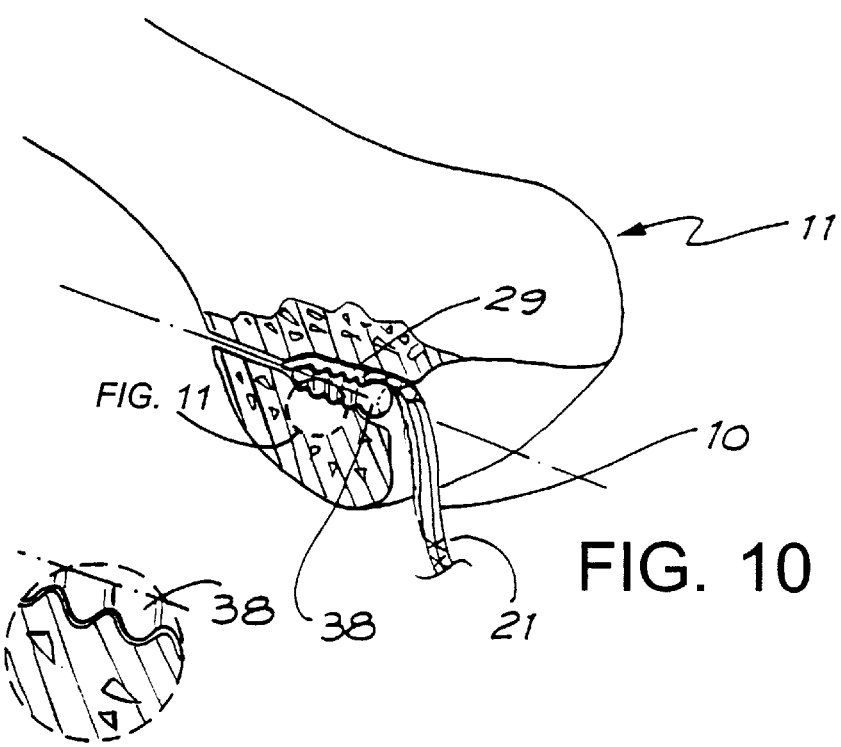
FIG. 10
FIG. 11

METHOD FOR SOFT TISSUE RECONSTRUCTION

This application is a continuation of application Ser. No. 08/614,904, filed on Mar. 13, 1996, now abandoned, which is a continuation of application Ser. No. 08/378,246, filed on Jan. 24, 1995, now abandoned.

FIELD OF THE INVENTION

The present invention relates to a method for the reconstruction of the anterior cruciate ligament of a patient. More particularly it relates to such a method in which a tendon graft is used to replace the ruptured anterior cruciate ligament.

BACKGROUND ART

As is well known the human knee comprises an articulation of the femur, the tibia and the patella. The femur and the tibia are maintained in a condition of stable articulation by a number of ligaments of which the principal ones are the anterior and posterior cruciate ligaments and the lateral ligaments. The rupture of the anterior cruciate ligament is relatively commonly encountered as a result of sporting injury or the like. This rupture leads to knee instability and can be a debilitating injury.

There have been a number of procedures designed to reconstruct the anterior cruciate ligament. Initially, attempts were made to replace the anterior cruciate ligament with tendons harvested from elsewhere in the body. These tendons were connected respectively to the femur and the tibia by staples, screws or the like inserted exteriorly into the bone and forming an external attachment to which the tendon could be connected externally of the bone. In some cases, the tendon passed over the top of one of the femoral condyles before attachment to the femur and in other cases a hole was drilled through the femur from outside the bone into the intercondylar notch. These attempts at anterior cruciate ligament reconstruction had mixed success. The tendon tended to break at its point of connection to the bone, or become loose over time, indicating that the tendon-bone interface was crucial for effective anterior cruciate ligament reconstruction.

These problems led to the use of bone-tendon-bone grafts generally harvested from mid-third patella tendon with a bone block at each end. Each bone block is inserted into an appropriate hole drilled in the femur or the tibia and secured in place by a screw driven between the wall of the hole and the bone block. While this system has been very successful in many respects a significant number of patients continue to have patella-femoral problems, especially over the mid-third patella tendon donor site.

In an effort to overcome these problems it has been proposed to suture hamstring tendon to a bone block derived from coring the tibial tunnel and to thereby manufacture a bone/tendon/bone graft similar to a mid-third patella tendon graft. The present inventors have found that the bone quality is extremely variable. This results in poor fixation and poor intra-operative pull-out strength in some cases. This procedure was also found to be a very demanding surgical procedure, and therefore difficult to reproduce.

DISCLOSURE OF THE INVENTION

The present invention consists in a method for the reconstruction of the anterior cruciate ligament of a patient comprising the steps of:

a) forming a tendon graft from tendon, other soft tissue or artificial tendon;

b) forming a hole through the patient's femur from a suitable point in the intercondylar notch therein anteriorly and laterally, the cross-sectional area of at least an end portion of the hole through the femur adjacent the intercondylar notch being sufficient to receive an end of the tendon graft and a suitable screw, peg or other fixation device having a leading end and a trailing end;

c) forming a suitably positioned hole through the patient's tibia opening at one end adjacent the cross-sectional medial tibial spine of the tibia of an area sufficient to receive the other end of the tendon graft;

d) drawing one end of the tendon graft into the enlarged end portion of the hole in the femur and simultaneously or sequentially drawing the other end of the tendon graft into the hole in the tibia;

e) inserting the leading end of a fixation device into the hole in the femur from the intercondylar notch end thereof until the trailing end of the fixation device is at least adjacent that end of the hole, and the tendon graft is pressed directly and firmly against a sidewall of the hole in the femur by the fixation device; and f) after tensioning the tendon graft appropriately, securing the other end of the tendon graft to the tibia.

It has been surprisingly found that, even without the presence of a bone block, a screw or other similar fixation device can adequately secure the tendon graft in place in both the femoral hole and the tibial hole. The initial pull out strength is high and with time permanent fixation is achieved through bone ingrowth into the tendon graft.

In a preferred embodiment of the invention the tendon graft comprises tendon or tendons derived from the hamstring tendons of the patient or from the achilles tendons of cadavers. Most preferably, the tendons are the semitendonosus and gracilis tendons of the patient harvested from the same leg as has the deficient anterior cruciate ligament. The invention could be practised using artificial tendon material or other bodily soft tissue such as ligament. Suitable synthetic plastics materials have been proposed for use in biological applications and could be used in place of natural tendon.

The tendon or tendons forming the tendon graft are preferably doubled over about their mid-point and trimmed to a desired length. The doubled over end and the free ends are preferably then each bound together over a length approximately equal to the length of the tendons that will extend through the holes in the femur and the tibia. Preferably, the ends of the tendon or tendons will be bound together using a Krakow suture or modified baseball stitch. A suture may also be connected to the tendon graft at each end. This suture may be used to draw the tendon graft through the respective holes and to tension the tendon graft prior to insertion of the fixation device in the tibial hole.

It is preferred that the hole in the femur is initially drilled as a guide hole of sufficient diameter to receive a suitable guide pin. The hole is then enlarged at least to a depth sufficient to receive an end portion of the tendon graft. This enlargement may be carried out using a cannulated drill guided on the guide pin. It is preferred, however, that the hole is enlarged using a rotary awl that enlarges the hole by compressing or compacting the bone around the original hole. It is particularly preferred that the size of the enlarged portion of the hole is sized to the size of the tendon graft to be placed in the hole. The cross-section area of the hole is desirably equal to or only very slightly greater than the cross-sectional area of the end portion of the tendon graft to be placed in the hole. If the fixation device has an enlarged head at its trailing end, it is desirable that the femoral hole has adjacent the intercondylar notch a short section of further increased cross-sectional area to receive the head of the fixation device. Similarly it is preferred that the external end of the tibial hole has a short section of further increased cross-sectional area.

The tibial hole is preferably formed by drilling a hole having a cross-sectional area just sufficient to receive the other end portion of the tendon graft. As the tendon graft may vary in cross-sectional area along their length it is usual to position the larger end of the tendon or tendons in the tibial hole. A guide hole is preferably drilled from the outside and is guided so that at its exit from the tibia it will be at the coronal level of the median tibial eminence ⅔ of the way across the notch, lateral to medial, so as to remove the anterior cruciate ligament stump. The aim of positioning is so that the final hole causes the graft to arise from the center of the notch coronally, sufficiently posterior to avoid impingement with the roof of the notch at full extension of the knee. The point of entry into the tibia is preferably selected such that the length of the hole is just sufficient to receive the other end portion of the tendon or tendons when the one end has been secured in the femoral hole. A guide pin is preferably placed through this guide hole and the hole enlarged to the desired cross-sectional area by a cannulated rotary awl guided along the guide pin.

In another aspect the present invention consists in a method for forming a hole in bone comprising the steps of
 a) drilling a guide hole in the bone;
 b) inserting a guide wire into the guide hole, and
 c) passing a cannulated rotary awl down the guide wire while causing the awl to rotate to enlarge the guide hole to a desired size by compressing or compacting the bone around the guide hole.

The one end of the tendon graft is preferably drawn into the femoral hole by a suture that is connected to one end of the tendon or tendons and is positioned to extend through the tibial hole, through the knee joint, through the femoral hole and out of the patient's thigh. As the suture is pulled, the tendon graft is drawn through the tibial hole into the femoral hole. Using this method when the one end of the tendon graft is firmly drawn into the enlarged portion of the femoral hole the other end of the tendon graft will be just drawn into the outside of the tibial hole.

The tendon graft is preferably fixed in the femoral hole by being directly and firmly pressed against the sidewall of the hole by a screw. The screw is most preferably formed with a thread devoid of an outermost cutting line so that neither the tendon or tendons nor the suture stitches around them will be cut by a sharp thread on the screw. The screw preferably also has a hemispherical head and is placed in the hole anteriorly of the tendon graft. This causes the tendon graft to firstly be spread as an arc around a posterior part of the circumferences of the screw and secondly causes the tendon graft to be curved smoothly around the head as it exits the femoral hole. Instead of a screw the tendon graft may be held in place in the femoral hole by a suitable pin, peg or other device that will force the tendon graft directly and firmly against the sidewall of the femoral hole. The head of the screw, pin, peg or the like should preferably be just below the surface of the femur. This ensures that the tendon graft is pressed against the sidewall of the femoral hole up to the condylar notch end of the hole. This prevents "pistoning", i.e. movement under cyclic load of the tendon or tendon bundle longitudinally of the hole, of the tendon graft in the hole as happened with many prior art systems. This "pistoning" of the tendon or tendon bundle prevents bone ingrowth into the tendon graft and therefore hinders the permanent fixation of the tendon to the bone.

After the one end of the tendon graft is secured in the femoral hole a suture connected to the other end of the tendon graft is drawn tight and a suitable screw, pin, peg or the like is preferably inserted into the tibial hole from its outside end. The length of the screw, pin, peg or the like is preferably of such a length that, when its head is inserted until it is just below the outside surface of the tibia, it will extend substantially the full length of the tibial hole. The screw, pin or peg in the tibial hole the tibial hole serves to force the other end of the tendon graft into direct and firm contact with the side wall of the tibial hole. The tibial end of the tendon graft may, alternatively, be held in place by an exterior fixing such as a staple.

BRIEF DESCRIPTION OF THE DRAWINGS

FIG. 9 is a schematic perspective view showing the placement of a screw to secure the other end of the tendon graft in the tibial hole; and FIG. 10 is a vertical sectional view of a screw positioned in the femoral hole and securing the one end of the tendon graft.

FIG. 11 is an enlarged view of the portion of FIG. 10 enclosed by the circle in dashed lines.

BEST MODE OF CARRYING OUT THE INVENTION

Operating Protocol

Figure 1:
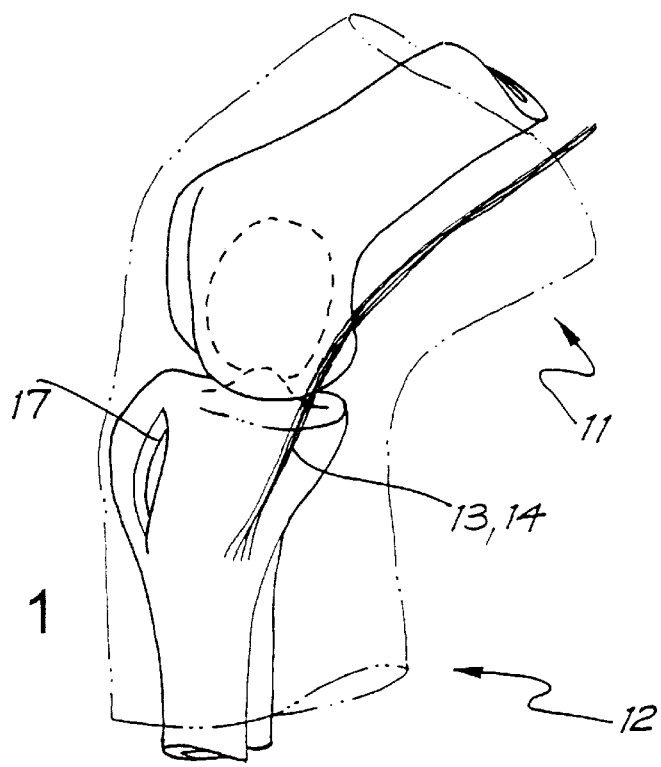
FIG. 1 is a schematic perspective view of a patient's knee showing the position of the semitendonosus and gracilis tendons and the incision through which it is harvested.
Figure 2:
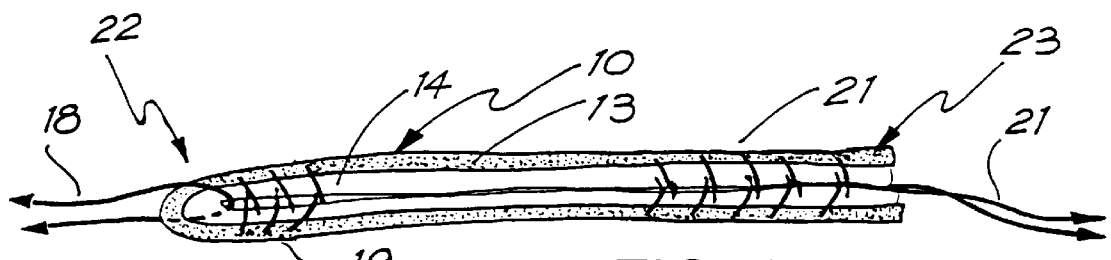
FIG. 2 is a perspective view of the harvested tendon prepared as a graft construct.
Figure 3:
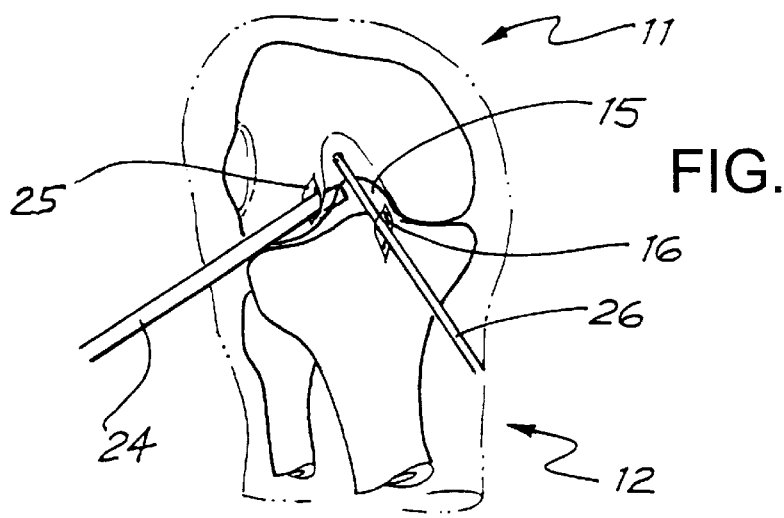
FIG. 3 is schematic perspective view of the patient's knee showing the positioning of an arthroscope and the drilling of a guide hole for the formation of a femoral hole to receive one end of the tendon graft.
Figure 4:
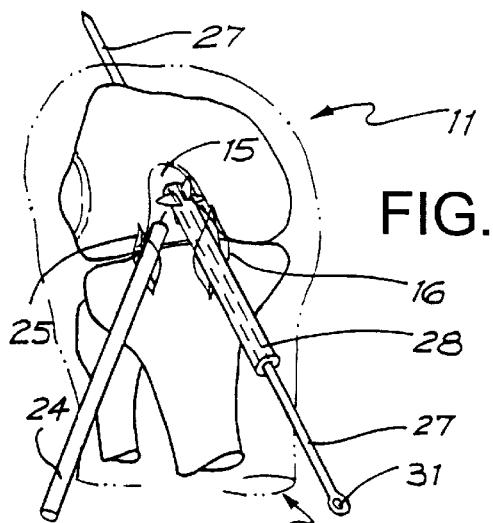
FIG. 4 is a schematic perspective view showing a cannulated awl on a beath pin being used to form the enlarged femoral hole.
Figures 5, 5A, 5B:
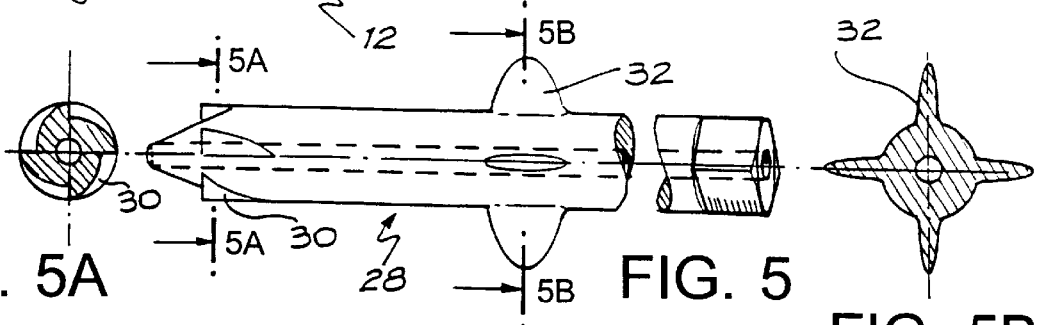
FIG. 5 is of an enlarged perspective view of the cannulated awl used in the procedure depicted in FIG. 4 including cross-sectional views along sections A—A and B—B.
Figure 6:
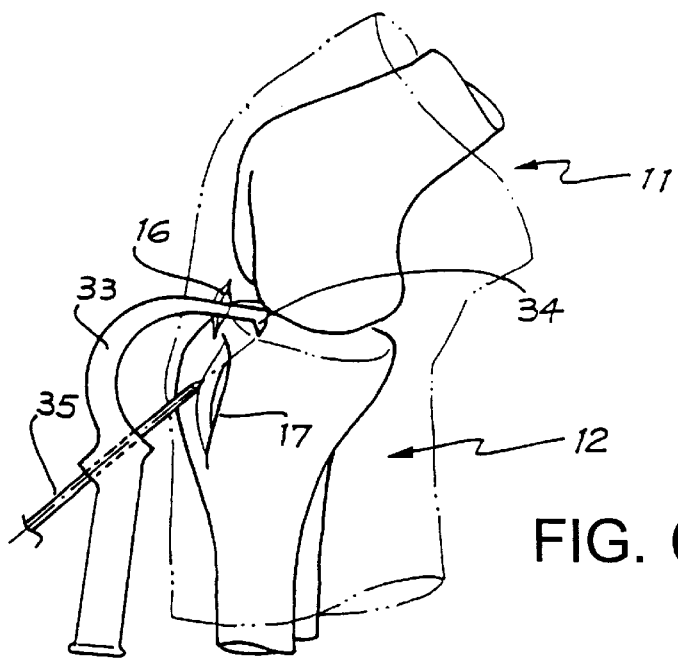
FIG. 6 is a schematic perspective view showing the drilling of a guide hole for a tibial hole to receive the other end of the tendon graft.
Figure 7:
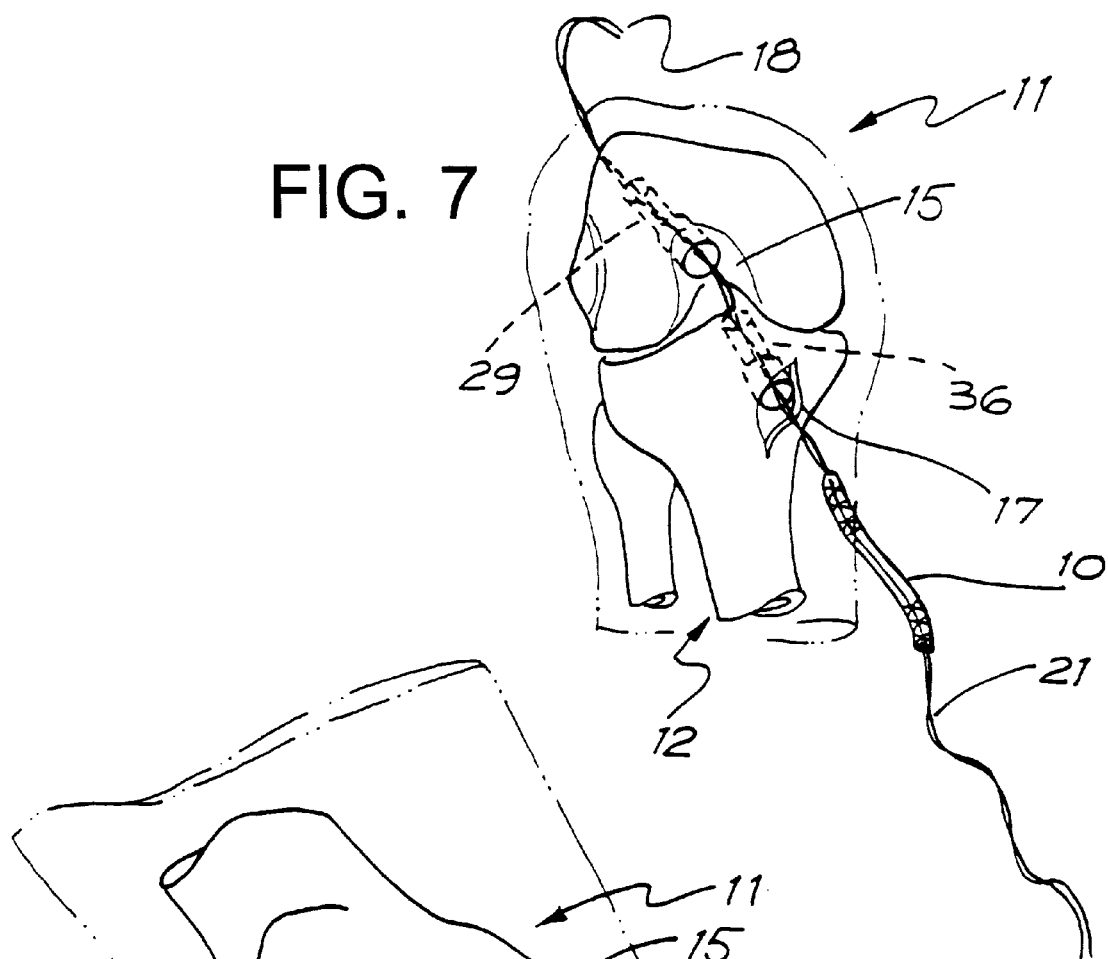
FIG. 7 is schematic perspective view of drawing the tendon graft through the tibial hole into the femoral hole.
Figure 8:
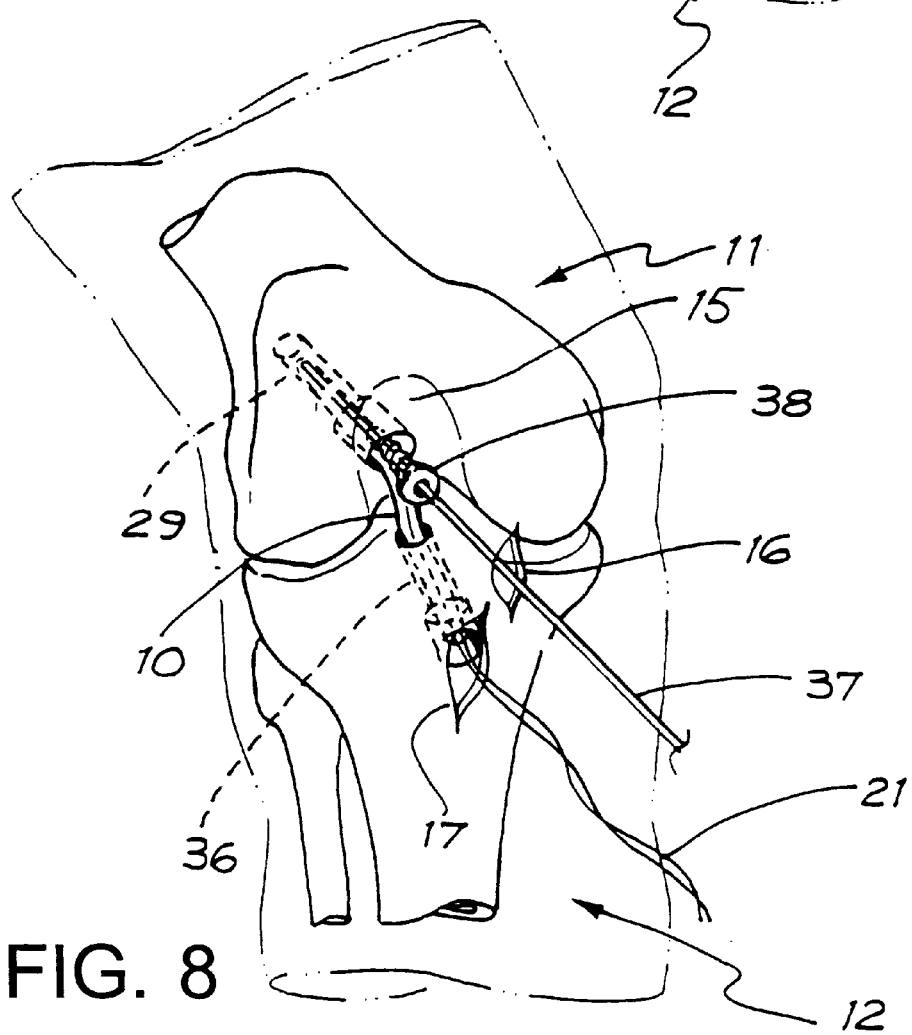
FIG. 8 is a schematic perspective view showing the placement of a screw to secure the one end of the tendon graft in the femoral hole.

The following protocol assumes the operator will be securing the graft 10 on the femoral side 11 from within the joint and on the tibial side 12 externally. The graft 10 consisting of semitendonosus and gracilis tendons 13 and 14 respectively is also assumed.

Preparation

Routine arthroscopy is performed prior to commencement of reconstruction of the anterior cruciate ligament. Portal placement is critical and can be described thus: the anterolateral portal (not shown) is towards the top of the lateral triangle soft spot. It is made with a transverse stab incision, aimed at the intercondylar notch 15. The anteromedial portal 16 is lower than usual, being 1 cm above the joint line and at the fat pad reflection, with the blade aimed slightly up and towards the intercondylar notch.

At this time, using the arthroscope in the anterolateral portal, any meniscal repair or excision is carried out as well as any debridement required for adequate visualisation of the joint in general and the notch in particular. Often this requires partial excision of the fat pad and particularly careful clearing of the notch surface of the lateral condyle of the femur. The scar tissue associated with the ruptured cruciate, the stump of the anterior cruciate ligament and the plica interarticularis should also be debrided. A curette is used to clear the lateral wall of the notch and a suction shaver may be used to remove the resultant debris.

The semitendonosus and gracilis tendons 13 and 14 are then harvested as graft material. This should be done in whatever fashion the operator is comfortable with, however, a single incision 17 approximately 30 millimeters is all that is required. The incision is medial to the tibial tubercle at the level of the pes anserine insertion. The harvesting of the semitendonosus and gracilis tendons 13 and 14 should result in at least 22 cm of the tendons. Separation of the tendon should occur at the musculo-tendinous junction. Care should be taken in harvesting the tendons to ensure the accessory distal insertions of the semitendonosus in particular are divided and do not divert the harvesting tool into the body of the tendon.

After the tendons 13 and 14 are cleared of adherent muscle fibers their length should be measured and the mid-point determined, ideally this is 11 cm from the distal insertion of the tendons. The broad surface of the semitendonosus 13 is wrapped around the tendon mass using this tendon to give a smooth exterior surface to the graft 10. The two tendons 13 and 14 are then doubled over a No. 5 suture 18 which will subsequently act as a lead pulling suture. With the tendons doubled over this lead suture by a clip on the free end (not shown), a No. 1 ethybond suture 19 is inserted into the folded end. The four strand hamstring tendon complex 10 is sutured with a modified double baseball stitch to hold them together so that they resist damage upon interference fit screw insertion. The femoral insertion end 22 should consist of at least 3 stitches securing the whole of the tendon mass for a length of 20 mm. At the free and tibial insertion end 23 of the tendons 10 another suture 21 is used along approximately 30 mm of length, again, in a modified double baseball stitch pattern. The 11 cm long 4 strand tendon graft 10 has now been constructed.

A mark is now made, using a sterile marking pen, on the tendon graft 30 mm distal to the double folded end of the tendon graft complex. This mark is used to ensure the tendon graft will be pulled up sufficiently into the femoral drill hole. The diameter of the tendon graft is now measured at both the proximal and distal ends, using a tube gauge. These diameters are noted for appropriate awl sizing. Any free tissue in the graft 10 which may bunch up and obstruct the passing of the graft 10 through the tibial and femoral drill holes should now be noted and excised.

Having taken the graft, the arthroscope 24 is then inserted into a central portal through a stab incision 25 over the patella tendon, just below the inferior pole of the patella (not shown), thereby allowing better visualisation of the back of the notch 15. Often it is found that further clearing of the lateral wall of the notch 15 is required. This should be performed until the capsular attachment is clearly visualised and palpated with a probe.

Femoral Drilling

A point 30° from the top of the notch (11 o'clock in a right knee; 1 o'clock in a left knee) and 5 mm from the back of the notch 15 on the lateral wall is then identified and indented with a burr. Care must be taken to avoid identifying the ridge of the anterior edge of the original ACL attachment as the back of the notch (resident's ridge). This error will lead to the femoral tunnel being too anterior, compromising graft function. A 4.5 mm drill 26 is then passed into the joint through the medial portal 16 and the tip placed in the burr hole while the knee is held at 90° (the use of standard tissue protecting sleeves is recommended). The drill is then spun a few turns to bed it into this depression.

Holding the drill tip in the shallow hole thus created the knee is pushed into as much flexion as it will achieve. Directing the drill approximately 20° anteriorly and 30° laterally with respect to the femur, a guide hole is then made, with drilling ceasing as soon as the outer cortex is felt to have been pierced. Withdraw the drill 26 and inspect the hole 29 to confirm position by passing the arthroscope deep into the notch.

With the knee at 90° flexion, a beath pin 27 is then passed through the medial portal and up to the entrance of the guide drill hole under direct vision. Care should be taken not to pass the pin 27 through the posterior cruciate ligament. The knee is flexed maximally and the pin 27 is passed up the guide hole and out through the skin. This pin 27 serves as the guide for a cannulated stepped awl 28. With the knee held fully flexed a stepped awl 28 of minor diameter matching the tendon graft, is then passed along the pin 27 and, under direct vision, the femoral hole 29 made. The stepped awl 28 has a diameter which corresponds to that of the measured tendon graft, and cutting ears 32 which are 25 mm distal from the tip (9 or 10 mm diameter) and 10 mm in length, to accommodate the screw head at the graft origin. Drilling should continue up to a mark just distal to the cutting ears 32. The awl 28 is formed with flutes 30 at its leading end that compact the bone surrounding the hole to enlarge it.

The awl 28 is then removed and a nylon loop (not shown) threaded into the eye 31 of the beath pin 27. With the loop end held, the pin 27 is drawn out of the femur and the free ends of the nylon and drawn through the femoral hole 29 and out of the thigh. Smoothing of the edge of the femoral hole and debridement of any loose issue is now carried out.

The tibial hole is then made with the use of a guide 33. The tip 34 of the guide 33 is passed through the anteromedial portal 16 and placed on a line from the anterior horn of the lateral meniscus to the medial tibial spine and medially, one quarter of the way across the intercondylar notch, that is just medial to the medial tibial spine. The drill guide 33 then passes through the distal skin incision 17 used for the harvesting of the hamstring tendon graft 10 and measures 40–45 mm distal from the cruciate ligament tibial attachment. The 4.5 mm drill 35 is used to establish the line until the cortex of the tibial plateau is reached, whereupon the guide is removed and the drilling completed under direct vision. The final position may be find tuned by hand, so that the final drill position will abut the medial eminence and remove the anterior cruciate ligament stump. Having achieved satisfactory placement of the 4.5 mm drill 35, a 2.0 mm guide wire (not shown) is passed into the hole. The guide wire should intersect the PCL near its femoral insertion to indicate correct drill hole placement and alignment. A cannulated awl (not shown but similar to awl 28) of minor diameter equal to that of the tendon graft's distal end can now be introduced over the guide wire. Drilling of the tibial hole 36 should continue up to a marker just distal to the cutting ears. When tibial hole enlargement is completed, the soft tissue at the entry to the joint can be cleared with a shaver.

With the knee at 90° flexion, a pair of grasping arthroscopy forceps (not shown) are then passed through the tibial drill hole until the jaw of the forceps is around the nylon threads previously passed through the joint. The looped end of the thread is then pulled through the tibial drill hole 36. The thread now passes through the tibial and femoral drill holes and is used to pass the leading graft thread 18. The threads 18 from the tendon graft 10 are placed through the lead thread loop and pulled proximally. Using these threads 18, the graft 10 is drawn into the joint and then into the femoral hole 29 until the mark made earlier, 30 mm from the doubled end 22 of the graft 10, is at the entrance to the femoral drill hole 29. Care should be taken as the graft 10 is pulled up that the distal insertion of the tendon graft 10 is not preventing the graft from passing up the tibial hole 36. Some degree of release may be required to achieve complete passage of the graft. A guide wire 37 is then introduced through the anteromedial portal 16 and the tip placed at the femoral hole 29 entrance, between the edge of the hole and the tendon graft 10. The knee is then fully flexed and the guide wire 37 runs up 25 mm into the tunnel between the graft 10 and the femoral hole 29 wall.

Once the surgeon is satisfied that the graft 10 and the wire 37 are correctly placed, by direct vision, a Donjoy RCI screw (made according to U.S. Pat. No. 5,383,878 38 and a driver (not shown) are run over the wire 37 and into the joint. Once the tip of the screw 38 is engaged between the graft 10 and the bone surface a firm tap with a mallet to encourage thread grip and to bed the graft down into the hole may be used, while the proximal threads 18 and the distal threads 21 on the graft 10 are kept taut, minimizing the tendency of the screw to wind up the graft 10. Then maintaining traction on the threads 18 and 21 used to hold the graft in the femoral drill hole 29, the screw 38 is advanced until the head is completely within the femoral hole 29. The head of the screw should be completely buried within the hole 29 and not visible once the screwdriver is removed. Should the screw not be advancing as it is rotated, it should again be tapped with a mallet to re-establish bony interlock and free any obstruction to its progress prior to continuing to screw in. With the knee still fully flexed the guide wire 37 is removed, once the surgeon is comfortable with the fixation and placement of the screw 38.

Having fixed the femoral end of the tendon graft 10, the knee is placed at 90° flexion and the tibial end 23 drawn down firmly, thereby applying tension to the graft 10. Isometricity may be tested at this time as the knee is extended and flexed. Having achieved the desired tension and positioning of the graft 10 a guide wire 39 is inserted between the graft and the bone of the tibia inferiorly. While maintaining distal tension on the graft 10, and holding the knee at 30–45° of flexion, a screw 41 similar to screw 38 is advanced until a partial grip is obtained. The knee is then gently extended to 0° and the screw 41 then advanced fully until the head is in the femoral hole 36 and a firm interference grip is achieved. Full extension must be achieved prior to completion of the insertion of the screw 41. The guide wire 39 is then removed.

The motion of the knee, Lachman test, anterior draw and pivot shift test are finally checked. The knee is copiously irrigated to remove debris. A drain is passed into the joint using the arthroscopic procedure and directly laterally.

Routine closure and post-operative care is followed.

What is claimed is:

1. A method for the reconstruction of an anterior cruciate ligament of a patient comprising the steps of:
    a) forming a graft of soft material from tendon, other soft tissue or artificial tendon or ligament;
    b) forming a first hole through a femur of the patient from a suitable point in an intercondylar notch therein anteriorly and laterally, wherein a cross-sectional area of at least an end portion of the first hole through the femur adjacent: the intercondylar notch is sufficient to receive a first end of the graft and a fixation screw device having a leading end and a trailing end;
    c) forming a suitably positioned second hole through a tibia of the patient, said second hole opening at one end adjacent to a medial spine of the tibia, and said second hole having a cross-sectional area sufficient to receive a second end of the graft;
    d) drawing the first end of the graft into the end portion of the first hole in the femur and drawing the second end of the graft into the second hole in the tibia;
    e) inserting the leading end of the fixation screw device into the first hole in the femur from said end portion of said first hole so that the fixation screw device engages the soft material of the graft and presses the soft material of the graft directly and firmly against a sidewall of the first hole in the femur; and
    f) securing the second end of the graft to the tibia.

2. A method for the reconstruction of the anterior cruciate ligament of a patient as claimed in claim 1 further comprising forming the graft from a tendon or tendons harvested from the patient or from a third party.

3. A method for the reconstruction of the anterior cruciate ligament of a patient as claimed in claim 2, further comprising forming the graft from a tendon derived from hamstring tendons of the patient.

4. A method for the reconstruction of the anterior cruciate ligament of a patient as claimed in claim 3, further comprising forming the graft from gracilis and semitendinosus tendons of the patient derived from a leg of the patient that contains said anterior cruciate ligament.

5. A method for the reconstruction of the anterior cruciate ligament of a patient as claimed in claim 4, further comprising doubling over the tendon or tendons and trimming the tendon or tendons to a desired length.

6. A method for the reconstruction of the anterior cruciate ligament of a patient as claimed in claim 1, in which the graft includes two free ends, and further comprising binding together each of the free ends of the graft over a length approximately equal to the length that the respective free ends of the graft will extend through the first and second holes.

7. A method for the reconstruction of the anterior cruciate ligament of a patient as claimed in claim 1, further comprising forming the first hole in the femur and/or the second hole in the tibia by drilling a guide hole, inserting a guide wire into the guide hole and passing a cannulated rotary awl down the guide wire to enlarge the guide hole to the desired cross-sectional size by compressing or compacting bone surrounding the guide hole.

8. A method for the reconstruction of the anterior cruciate ligament of a patient as claimed in claim 7, further comprising causing the rotary awl to form adjacent one end of the first hole and/or the second hole a short region of further increased cross-sectional area adapted to receive a head formed at the trailing end of the fixation screw device.

9. A method for the reconstruction of the anterior cruciate ligament of a patient as claimed in claim 1, wherein said anterior cruciate ligament is associated with a leg having a knee joint and a thigh, further comprising drawing the first end of the graft into the first hole and the second hole by a suture that is connected to the first end of the graft and extends through the second hole, the knee joint, the first hole and out the thigh.

10. A method for the reconstruction of the anterior cruciate ligament of a patient as claimed in claim 1, further comprising securing the second end of the graft to the tibia using a second fixation screw device having a leading end and a trailing end in accordance with the step of:

inserting the leading end of the second fixation screw device into an end of the second hole so that the second fixation screw device engages the soft material of the graft and presses the soft material of the graft directly and firmly against a sidewall of the second hole in the tibia.

11. A method for the reconstruction of the anterior cruciate ligament of a patient as claimed in claim 10, in which the second fixation screw device is cannulated.

12. A method for the reconstruction of the anterior cruciate ligament of a patient as claimed in claim 11, in which the second fixation screw device has a screw thread which is devoid of an outermost cutting line.

13. A method for the reconstruction of the anterior cruciate ligament of a patient as claimed in claim 12, in which the screw thread of the second fixation screw device is substantially nontapered.

14. A method for the reconstruction of the anterior cruciate ligament of a patient as claimed in claim 11, in which the second fixation screw device has a hemispherical head at the trailing end thereof.

15. A method for the reconstruction of an anterior cruciate ligament of a patient as claimed in claim 10, further comprising inserting the second fixation screw device until the trailing end thereof is adjacent the end of the second hole.

16. A method for the reconstruction of the anterior cruciate ligament of a patient as claimed in claim 15, wherein the step of inserting the second fixation screw device into the second hole includes driving the second fixation screw device into said second hole until the trailing end of said second fixation screw device is just within said second hole.

17. A method for the reconstruction of an anterior cruciate ligament of a patient as claimed in claim 1, further comprising inserting the fixation screw device until the trailing end thereof is adjacent the end of the first hole.

18. A method for the reconstruction of the anterior cruciate ligament of a patient as claimed in claim 17, wherein the step of inserting the fixation screw device into the first hole includes driving the fixation screw device into the hole until the trailing end of said fixation screw device is just within said first hole.

19. A method for the reconstruction of the anterior cruciate ligament of a patient as claimed in claim 1, in which the fixation screw device is cannulated.

20. A method for the reconstruction of the anterior cruciate ligament of a patient as claimed in claim 19, in which the fixation screw device has a screw thread which is devoid of an outermost cutting line.

21. A method for the reconstruction of the anterior cruciate ligament of a patient as claimed in claim 20, in which the fixation screw device has a hemispherical head at the trailing end thereof.

22. A method for the reconstruction of the anterior cruciate ligament of a patient as claimed in claim 20, in which the screw thread of the fixation screw device is substantially nontapered.

23. A method for the attachment of a graft of soft material to a bone of a patient at a joint between the bone and a second bone, wherein the soft material consists of a tendon or ligament or an artificial tendon or ligament, comprising the steps of:

a) forming a hole in said bone wherein a cross-sectional area of an end portion of the hole adjacent to the joint with the second bone is large enough to receive an end of the graft and a fixation screw device having a leading end and a trailing end;

b) drawing one end of the graft into the end portion of said hole; and c) inserting the leading end of the fixation screw device into the end portion of said hole from the joint so that the fixation screw device engages the soft material of the graft and presses the soft material of the graft directly and firmly against a sidewall of said hole in said bone.

24. The method set forth in claim 23, wherein a second bone is adjacent to said bone, and further including the steps of:

a) forming a second hole in said second bone wherein a cross-sectional area of an end portion of the second hole is large enough to receive an opposite end of the graft and a second fixation screw device having a leading end and a trailing end;

b) drawing the opposite end of the graft into the end portion of said second hole; and c) inserting the leading end of the second fixation screw device into said second hole so that the second fixation screw device engages the soft material of the graft and presses the soft material of the craft directly and firmly against a sidewall of said second hole in said second bone.

25. A method for the attachment of soft tissue associated with two adjacent bones of a patient as claimed in claim 24 wherein said first bone is a femur, said second bone is an adjacent tibia.

26. A method for the attachment of soft tissue as claimed in claim 24, further comprising forming said first hole in said first bone and/or said second hole in said second bone by drilling a guide hole, inserting a guide wire into the guide hole and passing a cannulated rotary awl down the guide wire to enlarge the guide hole to the desired cross-sectional size by compressing or compacting bone surrounding the guide hole.

27. A method for the attachment of soft tissue as claimed in claim 26, further comprising causing the rotary awl to form adjacent one end of said first hole in said first bone and/or said second hole in said second bone a short region of further increased cross-sectional area adopted to receive a head formed at the trailing end of the fixation screw device.

28. A method for the attachment of soft tissue as claimed in claim 24, in which the graft of soft material includes two free ends, and further comprising binding together each of the free ends of the soft material over a length approximately equal to the length that the respective free ends will extend into or through said hole in the first-mentioned bone and said second hole in the second bone.

29. The method set forth in claim 24 wherein said method is used for the reconstruction of an anterior cruciate ligament of a patient and said bone is a femur in the patient, and said second bone is a tibia in the patient; and further comprising forming said hole from a suitable point in an intercondylar notch in said femur anteriorly and laterally, and forming said second hole through the tibia and open at one end adjacent a medial spine of the tibia.

30. The method set forth in claim 23 wherein said method is used for the reconstruction of an anterior cruciate ligament of a patient and said bone is a femur in the patient, and further comprising forming said hole from a suitable point in an intercondylar notch in said femur anteriorly and laterally.

31. A method for the attachment of soft tissue as claimed in claim 23, wherein said fixation screw device is cannulated.

32. A method for the attachment of soft tissue as claimed in claim 23 further comprising forming the graft of soft material from a tendon or tendons harvested from a patient or from a third party.

33. A method for the attachment of soft tissue as claimed in claim 32, further comprising doubling over the tendon or tendons and trimming the tendon or tendons to a desired length.

34. The method set forth in claim 23, in which the fixation screw device is cannulated.

35. The method set forth in claim 34, in which the fixation screw device has a screw thread which is devoid of an outermost cutting line.

36. The method set forth in claim 35, in which the fixation screw device has a hemispherical head at the trailing end thereof.

37. The method set forth in claim 35, in which the screw thread of the fixation screw device is substantially nontapered.

38. The method set forth in claim 24, in which the second fixation screw device is cannulated.

39. The method set forth in claim 38, in which the second fixation screw device has a screw thread which is devoid of an outermost cutting line.

40. The method set forth in claim 39, in which the second fixation screw device has a hemispherical head at the trailing end thereof.

41. The method set forth in claim 39, in which the screw thread of the second fixation screw device is substantially nontapered.

* * * * *

UNITED STATES PATENT AND TRADEMARK OFFICE
CERTIFICATE OF CORRECTION

PATENT NO. : 6,235,057 B1
DATED : May 22, 2001
INVENTOR(S) : Roger et al.

It is certified that error appears in the above-identified patent and that said Letters Patent is hereby corrected as shown below:

Title page 2,
Item [56], References Cited, FOREIGN PATENT DOCUMENTS, replace "0 655 840" with -- 2 655 840 --.

Column 6,
Line 37, replace "32" with -- 32,--.

Column 8, claim 1,
Line 13, replace "adjacent:" with -- adjacent --.

Column 10, claim 24,
Line 36, replace "craft" with -- graft --.

Signed and Sealed this

Eighth Day of January, 2002

Attest:

JAMES E. ROGAN
Attesting Officer   Director of the United States Patent and Trademark Office